(12) United States Patent
Mao et al.

(10) Patent No.: US 6,919,427 B1
(45) Date of Patent: Jul. 19, 2005

(54) POLYPEPTIDE-RNA BINDING PROTEIN 33 AND POLYNUCLEOTIDE ENCODING SAID POLYPEPTIDE

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 355 days.

(21) Appl. No.: 10/111,109
(22) PCT Filed: Oct. 16, 2000
(86) PCT No.: PCT/CN00/00323
§ 371 (c)(1), (2), (4) Date: Apr. 22, 2002
(87) PCT Pub. No.: WO01/30818
PCT Pub. Date: May 3, 2001

(30) Foreign Application Priority Data
Oct. 22, 1999 (CN) ........................ 99119821 A (51) Int. Cl.[7] ............................................. A61K 38/00
(52) U.S. Cl. ........................ 530/325; 530/300; 514/12
(58) Field of Search ................................ 530/325, 300; 514/12

(56) References Cited

PUBLICATIONS

Boni et al. 1990 Ribosome–messenger recognition: mRNA target sites for ribosomal protien S1. Nucleic Acids Research, vol. 19:1:155–162.*

Science 282 (5396), 2012–1018 (1998). The *C. elegons* Genome Sequencing Consortium et al. 'Genome sequence of the nematode *C. elegans*: a platform for investigating biology. The *C. elegans* Sequencing Consortium.'

Science 274 (5287), 546 (1996), Goffeau, A. et al. 'Life with 6000 genes.'

* cited by examiner

Primary Examiner—Robert A. Wax
Assistant Examiner—Suzanne M. Mayer
(74) Attorney, Agent, or Firm—Crowell & Moring LLP (57) ABSTRACT

The invention discloses a new kind of RNA binding protein 33 and polynucleotide encoding the polypeptide and a process for producing the polypeptide by recombinant methods. It also discloses the method of applying the polypeptide for the treatment of various kinds of diseases, such as cancer, hemopathology, HIV infection, immune diseases and inflammation. The antibody and antagonist of the polypeptide and the therapeutic use of the same is also disclosed. In addition, it refers to the use of polynucleotide encoding said RNA binding protein 33.

5 Claims, 2 Drawing Sheets

Identity =142/258 (55%), Similarity= 183/258 (70%)

```
RNA binding      :   1  MQSDDVIWDTLGNKQFCSFKIRTKTQSFCRNEYSLTGLCNRSSCPLANSQYATIKEEKGQ   60
protein 33
                        MQ DDV W+ L NK  C++K  TK + FC+NE +LTGLCNR+SCPLANSQYAT++EE G nemathelminth    :   1  MQCDDVTWNIL-NKGQCAYKAWTKPKMFCKNEMNLTGLCNRASCPLANSQYATVREENGV  59
cDNA yk97f10.3

RNA binding      :  61  CYLYMKVIERAAFPRRLWERVRLSKNYEKALEQIDENLIYWPRFIRHKCKQRFTKITQYL 120
protein 33 nemathelminth    :  60  CYLYAKVVERSHYPRRLWEKTKLSKDMNKALEQISDQLLHWSEYVRHKCKARLIRIHQYL 119
cDNA yk97f10.3
                        CYLY KV+ER+ +PRRLWE+ +LSK+  KALEQI + L++W ++RHKCK R  +I QYL RNA binding      : 121  IRIRKLTLK-RQRKLVPLSKKVERREKRREEKALIAAQLDNAIEKELLERLKQDTYGDIY 179
protein 33
                        IR+RK+ ++   Q+KL+P+ +KVERREKRREEKAL+AA+LD+AIEKELL RLKQ TYGD+Y nemathelminth    : 120  IRMRKMAVRGNQKKLIPIGRKVERREKRREEKALVAAKLDHAIEKELLARLKQGTYGDVY 179
cDNA yk97f10.3

RNA binding      : 180  NFPIHAFDKALEQQEAESDSSDTEEKDDDDDEEDVGKREFVEDGEVDESDISDFEDMDK  239
protein 33
                        NF   AF++ LE  E E +    E+DD    D G+ +FV D     D SD ED D nemathelminth    : 180  NFRQEAFEQMLENTEKELEVEQELEQDD-----ADTGETQFVAD-----FDSSDDEDQDM 229
cDNA yk97f10.3

RNA binding      : 240  LDASSDEDQDGKSSSEEEE                                          258
protein 33
                         D            G + SE E+ nemathelminth    : 230  EDGGDGHWSPGDTDSENED 248                                      248
cDNA yk97f10.3
```

Identity =142/258 (55%), Similarity= 183/258 (70%)

```
RNA binding     :   1  MQSDDVIWDTLGNKQFCSFKIRTKTQSFCRNEYSLTGLCNRSSCPLANSQYATIKEEKGQ    60
protein 33             MQ DDV W+ L NK  C++K TK + FC+NE +LTGLCNR+SCPLANSQYAT++EE G
nemathelminth   :   1  MQCDDVTWNIL-NKGQCAYKAWTKPKMFCKNEMNLTGLCNRASCPLANSQYATVREENGV    59
cDNA yk97f10.3

RNA binding     :  61  CYLYMKVIERAAFPRRLWERVRLSKNYEKALEQIDENLIYWPRFIRHKCKQRFTKITQYL   120
protein 33             CYLY KV+ER+ +PRRLWE+ +LSK+  KALEQI + L++W ++RHKCK R  +I QYL
nemathelminth   :  60  CYLYAKVVERSHYPRRLWEKTKLSKDMNKALEQISDQLLHWSEYVRHKCKARLIRIHQYL   119
cDNA yk97f10.3

RNA binding     : 121  IRIRKLTLK-RQRKLVPLSKKVERREKRREEKALIAAQLDNAIEKELLERLKQDTYGDIY   179
protein 33             IR+RK+ ++  Q+KL+P+ +KVERREKRREEKAL+AA+LD+AIEKELL RLKQ TYGD+Y
nemathelminth   : 120  IRMRKMAVRGNQKKLIPIGRKVERREKRREEKALVAAKLDHAIEKELIARLKQGTYGDVY   179
cDNA yk97f10.3

RNA binding     : 180  NFPIHAFDKALEQQEAESDSSDTEEKDDDDDEEDVGKREFVEDGEVDESDISDFEDMDK   239
protein 33             NF   AF++ LE  E E +     E+DD         D G+ +FV D     D SD ED D
nemathelminth   : 180  NFRQEAFEQMLENTEKELEVEQELEQDD-----ADTGETQFVAD-----FDSSDDEDQDM   229
cDNA yk97f10.3

RNA binding     : 240  LDASSDEDQDGKSSSEEEE                                           258
protein 33             D        G + SE E+
nemathelminth   : 230  EDGGDGHWSPGDTDSENED                                           248
cDNA yk97f10.3
```

POLYPEPTIDE-RNA BINDING PROTEIN 33 AND POLYNUCLEOTIDE ENCODING SAID POLYPEPTIDE

FIELD OF INVENTION

The invention relates to the field of biotechnology. In particular, the invention relates to a novel polypeptide—RNA binding protein 33, and a polynucleotide sequence encoding said polypeptide. The invention also relates to the method for the preparation and application of said polynucleotide and polypeptide.

TECHNICAL BACKGROUND

RNA binding proteins are necessary for the growth and development of various cells. These proteins are involved in the splicing, editing, transporting and localizing of RNA, and mRNA post-transcription control. These proteins have special RNA binding domains so as to bind with RNA. Many conserved RNA binding motifs have been found by amino acid homology and structural similarity analysis on these RNA binding domains. These motifs include RNP motif, arginine rich motif, zinc finger motif, Y box, KH motif and double-stranded RNA binding motif, etc., and each of them has a special conservative sequence (Burd,C. G. and Dreyfuss,G. (1994) Science,265:615–621).

An RNP motif consists of about 90 amino acids, and h as two highly conservative regions. One is a hydrophilic fragment with 6 amino acid residues PNP-2 motif, the other is a motif with 8 amino acid residues RNP-1 or RNP-CS motif). The RNP domain exists in at least 25 kinds of proteins, including nonhomogeneous ribonucleoprotein (hnRNPA, hnRNPC, hnRNPE, hnRNPG, etc.), small molecular ribonucleoprotein (U1 SNRNPA, U2 snRNPB, etc.), pre-RNA and mRNA-related protein (for example, protein synthesis initiation factor 4B, nucleolin, polyA binding protein, etc.) and many other proteins (for example, *drosophila* sex-determing protein, Sx1 protein and Tra-2 protein, La antigen, 60 kd Ro protein, murine insulin induced responsive protein Cl-4, etc.

OBJECTIVES OF THE INVENTION

One objective of the invention is to provide an isolated novel polypeptide, i.e., an RNA binding protein 33, and fragments, analogues and derivatives thereof.

Another objective of the invention is to provide a polynucleotide encoding said polypeptide.

Another objective of the invention is to provide a recombinant vector containing a polynucleotide encoding RNA binding protein 33.

Another objective of the invention is to provide a genetically engineered host cell containing a polynucleotide encoding RNA binding protein 33.

Another objective of the invention is to provide a method for producing RNA binding protein 33.

Another objective of the invention is to provide an antibody against a RNA binding protein 33.

Another objective of the invention is to provide mimetics, antagonists, agonists, and inhibitors for the polypeptide of the RNA binding protein 33.

Another objecitve of the invention is to provide a method for the diagnosis and treatment of the diseases associated with an abnormality of RNA binding protein 33.

SUMMARY OF THE INVENTION

In the first aspect, the invention provides a novel isolated RNA binding protein 33 which is originated from human and comprises a polypeptide having the amino acid sequence of SEQ ID NO: 2, or its conservative mutants, or its active fragments, or its active derivatives and its analogues. Preferably, the polypeptide is a polypeptide having the amino acid sequence of SEQ ID NO: 2.

In the second aspect, the invention provides an isolated polynucleotide encoding said polypeptide, the polynucleotide comprises a nucleotide sequence that shares at least 70% homology to the nucleotide sequence selected from the group consisting of (a) the polynucleotide encoding said RNA binding protein 33; and (b) a polynucleotide complementary to the polynucleotide (a). Preferably, said nucleotide sequence encodes a polypeptide comprising the amino acid sequence of SEQ ID NO: 2. More preferably, said nucleotide sequence is selected from the group consisting of (a) the sequence of position 16–918 in SEQ ID NO: 1; and (b) the sequence of position 1–3473 in SEQ ID NO: 1.

In the third aspect, the invention provides a vector comprising said polynucleotide and a host cell transformed or transfected by said vector or directly transformed or transfected by said polynucleotide.

Other aspects of the invention are apparent to the skilled in the art in view of the disclosure.

BRIEF DESCRIPTION OF THE DRAWINGS

The following drawings are provided to illustrate the embodiment of the invention, not to limit the scope of invention defined by the claims.

DETAILED DESCRIPTION OF THE INVENTION

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated RNA binding protein 33" means that RNA binding protein 33 does not essentially contain other proteins, lipids, carbohydrate or any other substances associated therewith in nature. The skilled in the art can purify RNA binding protein 33 by standard protein purification techniques. Essentially the purified polypeptide forms a single main band on a non-reductive PAGE gel. The purity of RNA binding protein 33 polypeptide can be analyzed by amino acid sequence analysis.

The invention provides a novel polypeptide —RNA binding protein 33, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacteria, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of RNA binding protein 33. As used in the invention, the terms "fragment", "derivative" and "analogue" mean the polypeptide that essentially retains the same biological functions or activity of RNA binding protein 33 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, include a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 3473 bp, whose ORF (16–918) encodes 300 amino acids. Based on amino acid homology comparison, the encoded polypeptide is 55% homologous to nemathelminth cDNA yk97f10.3. This novel human RNA BINDING PROTEIN 33 has similar structures and biological functions to nemathelminth cDNA yk97f10.3.

The polynucleotide according to the invention may be in the forms of DNA or RNA. The forms of DNA include cDNA, genomic DNA, and synthetic DNA, etc., in single stranded or double stranded form. DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional coding sequence) plus the non-coding sequence.

The term "polynucleotide encoding the polypeptide" includes polynucleotides encoding said polypeptide and polynucleotides comprising additional encoding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2.

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in the amplification techniques of nucleic acid, such as PCR, so as to determine and/or isolate the polynucleotide encoding RNA binding protein 33.

The polypeptide and polynucleotide of the invention are preferably in the isolated form, preferably purified to be homogenous.

According to the invention, the specific nucleic acid sequence encoding RNA binding protein 33 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. A standard method for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Methods can be used for screening for the polynucleotide of the invention from cDNA library. These methods include, but are not limited to, (1) DNA—DNA or DNA-RNA hybridization; (2) the appearance or loss of the function of the marker-gene; (3) the determination of the level of RNA binding protein 33 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleocides, preferably at least 30 nucleocides, more preferably at least 50 nucleocides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by RNA binding protein 33 gene can be carried out by an immunology method, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various. DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a gentically engineered host cell transformed with the vector of the invention or directly with the sequence encoding RNA binding protein 33, and a method for producing the polypeptide of the invention by recombinant techniques.

In the present invention, the polynucleotide sequences encoding RNA binding protein 33 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of RNA binding protein 33 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of $E.$ $coli$; $P_L$ promoter of $\lambda$ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.$ $coli.$ The skilled in the art know clearly how to select appropriate vectors, transcriptional regulatory elements, e.g., promoters, enhancers, and selective marker genes.

According to the invention, polynucleotide encoding RNA binding protein 33 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as $E.$ $coli,$ $Streptomyces,$ $Salmonella$ $typhimurium$; fungal cells, such as yeast; plant cells; insect cells such as $Drosophila$ S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as $E.$ $coli$, competent cells, which are capable of DNA uptake, can be prepared from cells harvested after exponential growth phase and subsequently treated by the $CaCl_2$ method using procedures well known in the art. Alternatively, $MgCl_2$ can be used. Transformation can also be carried out by electroporation, if desired. When the host is an eukaryote, transfection methods as well as calcium phosphate co-precipitation method may be used. Conventional mechanical procedures such as microinjection, electroporation, or liposome-mediated transfection may also be used.

The recombinant RNA binding protein 33 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human RNA binding protein 33 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatagraphy, and a combination thereof.

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

The invention also provides methods for screening compounds so as to identify an agent which enhance RNA binding protein 33 activity (agonists) or decrease RNA binding protein 33 activity (antagonists). The agonists enhance the biological functions of RNA binding protein 33 such as inactivation of cell proliferation, while the antagonists prevent and cure the disorders associated with the excess cell proliferation, such as various cancers. For example, in the presence of an agent, the mammal cells or the membrane preparation expressing RNA binding protein 33 can be incubated with the labeled RNA binding protein 33 to determine the ability of the agent to enhance or repress the interaction.

Antagonists of RNA binding protein 33 include antibodies, compounds, receptor deletants and analogues. The antagonists of RNA binding protein 33 can bind to RNA binding protein 33 and eliminate or reduce its function, or inhibit the production of RNA binding protein 33, or bind to the active site of said polypeptide so that the polypeptide can not function biologically.

When screening for compounds as an antagonist, RNA binding protein 33 may be added into a biological assay. It can be determined whether the compound is an antagonist or not by determining its effect on the interaction between RNA binding protein 33 and its receptor. Using the same method as that for screening compounds, receptor deletants and analogues acting as antagonists can be selected. Polypeptide molecules capable of binding to RNA binding protein 33 can be obtained by screening a polypeptide library comprising various combinations of amino acids bound onto a solid matrix. Usually, RNA binding protein 33 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of RNA binding protein 33. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with RNA binding protein 33. Various adjuvants, including but are not limited to Freund's adjuvant, can be used to enhance the immunization. The techniques for producing RNA binding protein 33 monoclonal antibodies include, but are not limited to, the hybridoma technique (Kohler and Milstein. Nature,1975, 256:495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS,1985,81:6851). Furthermore, techniques for producing a single-chain antibody (U.S. Pat. No. 4,946,778) are also useful for preparing single-chain antibodies against RNA binding protein 33.

The antibody against RNA binding protein 33 can be used in immunohistochemical method to detect the presence of RNA binding protein 33 in a biopsy specimen.

The monoclonal antibody specific to RNA binding protein 33 can be labeled by radioactive isotopes, and injected into human body to trace the location and distribution of RNA binding protein 33. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to RNA binding protein 33 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill RNA binding protein 33-positive cells.

The antibody of the invention is useful for the therapy or the prophylaxis of disorders related to the RNA binding protein 33. The appropriate amount of antibody can be administrated to stimulate or block the production or activity of RNA binding protein 33.

The invention further provides diagnostic assays for quantitative and in situ measurement of RNA binding protein 33 level. These assays are well known in the art and include FISH assay and radioimmunoassay. The level of RNA binding protein 33 detected in the assay can be used to illustrate the importance of RNA binding protein 33 in diseases and to determine the diseases associated with RNA binding protein 33.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

RNA binding protein 33 polynucleotides also have many therapeutic applications. Gene therapy technology can be used in the therapy of abnormal cell proliferation, development or metabolism, which are caused by the loss of RNA binding protein 33 expression or the abnormal or non-active expression of RNA binding protein 33. Recombinant gene therapy vectors, such as virus vectors, can be designed to express mutated RNA binding protein 33 so as to inhibit the activity of endogenous RNA binding protein 33. For example, one form of the mutated RNA binding protein 33 is a truncated RNA binding protein 33 whose signal transduction domain is deleted. Therefore, this mutated RNA binding protein 33 can bind the downstream substrate without the activity of signal transduction. Thus, the recombinant gene therapy vectors can be used to cure diseases caused by abnormal expression or activity of RNA binding protein 33. The expression vectors derived from a virus, such as retrovirus, adenovirus, adeno-associated virus, herpes simplex virus, parvovirus, and so on, can be used to introduce the RNA binding protein 33 gene into the cells. The methods for constructing a recombinant virus vector harboring RNA binding protein 33 gene are described in the literature (Sambrook, et al. supra). In addition, the recombinant RNA binding protein 33 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the Translation of RNA binding protein 33 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding RNA binding protein 33 can be used in the diagnosis of RNA binding protein 33 related diseases. The polynucleotide encoding RNA binding protein 33 can be used to detect whether RNA binding protein 33 is expressed or not, and whether the expression of RNA binding protein 33 is normal or abnormal in the case of diseases. For example, RNA binding protein 33 DNA sequences can be used in the hybridization with biopsy samples to determine the expression of RNA binding protein 33. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for the analysis of differential expression of genes in tissues and for the diagnosis of genes. The RNA binding protein 33 specific primers can be used in RNA-polymerase chain reaction and in vitro amplification to detect the transcripts of RNA binding protein 33.

Further, detection of mutations in RNA binding protein 33 gene is useful for the diagnosis of RNA binding protein 33-related diseases. Mutations of RNA binding protein 33 include site mutation, translocation, deletion, rearrangement and any other mutations compared with the wild-type RNA binding protein 33 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice written by a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. RNA binding protein 33 is administered in an amount, which is effective for treating and/or prophylaxis of the specific indication. The amount of RNA binding protein 33 administrated on patient will depend upon various factors, such as delivery methods, the subject health, the judgment of the skilled clinician.

EXAMPLE

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

The Cloning of RNA Binding Protein 33

The total RNA from human embryo brain was extracted by one-step method with guanidinium isocyanate/phenol/chloroform. The poly(A) mRNA was isolated from the total RNA with Quik mRNA Isolation Kit (Qiegene). cDNA was prepared by reverse transcription with 2 ug poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 0196b12 was found to be a novel DNA sequence. The inserted cDNA sequence of clone 0196b12 was dual-directionally sequenced with a serial of synthesized primers. It was indicated that the full length cDNA contained in clone 0196b12 was 3473 bp (SEQ ID NO: 1) with a 903 bp ORF located in positions 16 bp–918 bp which encoded a novel protein (SEQ ID NO: 2). This clone was named pBS-0196b12 and the encoded protein was named RNA binding protein 33.

Example 2

Homology Search of cDNA Clone

The homology research of the DNA sequence and its protein sequence of RNA binding protein 33 of the invention were performed by Blast (Basic local Alignment search tool) [Altschul, SF et al. J. Mol. Biol.1990;215:403–10] in the databases such as Genbank, Swissport, etc. The most homologous gene to RNA binding protein 33 of the invention is known nemathelminth cDNA yk97f10.3. The Genbank accession number of its encoded protein is U41534. The alignment result of the protein was shown in FIG. 1. Two proteins are highly homologous with an identity of 46% and a similarity of 55%.

Example 3

Cloning RNA Binding Protein 33 Gene by RT-PCR

The template was total RNA extracted from embryo brain. The reverse transcription was carried out with oligo-dT primer to produce cDNA. After cDNA purified with Qiagen Kit, PCR was carried out with the following primers:

Primer1: 5'-GGAGCCGCGGACACCATGCAGTCGG-3' (SEQ ID NO: 3)

Primer2: 5'-CGCCGCTTAAGTTTTTTGTTTATTG-3' (SEQ ID NO: 4)

Primer1 is the forward sequence started from position 1 of 5' end of SEQ ID NO: 1.

Primer2 is the reverse sequence of the 3' end of SEQ ID NO: 1.

The amplification condition was a 50 ul reaction system containing 50 mmol/L KCl, 10 mmol/L Tris-Cl (pH8.5), 1.5 mmol/L $MgCl_2$, 200 mmol/L dNTP, 10 pmol of each primer, 1U Taq DNA polymerase(Clontech). The reaction on a PE 9600 DNA amplifier subjected to 94° C. 30 sec, 55° C. 30 sec, and 72° C. 2 min for 25 cycles. The β-actin was used as a positive control, and a blank template, as a negative control in RT-PCR. The amplified products were purified with QIAGEN kit, ard linked with pCR vector (Invitrogen) using TA Cloning Kit. The DNA sequencing results show that the DNA sequence of PCR products was identical to nucleotides 1–3473 bp of SEQ ID NO: 1.

Example 4

Northern Blotting of Expression of RNA Binding Protein 33 Gene

The total RNA was extracted by one-step method (Anal. Biochem 1987, 162, 156–159)with guanidinium isocyanate-phenol-chloroform. That is, homogenate the organize using 4M guanidinium isocyanate-25 mM sodium citrate, add 1 volume phenol and ⅕ volume chloroform-isoamyl alcohol (49:1), centrifuge after mixing. Take out the water phase, add 0.8 volume isopropyl alcohol, then centrifuge the mixture. Wash the RNA precipitation using 70% ethanol, then dry, then dissolve it in the water. 20 µg RNA was electrophoresed on the 1.2% agarose gel containing 20 mM 3-(N-morpholino) propane sulfonic acid(pH 7.0)-5 mM sodium acetate-imM EDTA-2.2 M formaldehyde. Then transfer it to a nitrocellulose filter. Prepare the $^{32}$P-labelled DNA probe with $\alpha$-$^{32}$P dATP by random primer method. The used DNA probe is the coding sequence (16 bp–918 bp) of RNA binding protein 33 amplified by PCR indicated in FIG. 1. The nitrocellulose filter with the transferred RNA was hybridized with the $^{32}$P-labelled DNA probe ($2\times10^6$ cpm/ml) overnight in a buffer containing 50% formamide-25 mM KH$_2$PO$_4$(Ph7.4)-5× Denhardt's solution and 200 µg/ml salmine. Then wash the filter in the 1×SSC-0.1% SDS, at 55° C., for 30 min. Then analyze and quantitative determinate using Phosphor Imager.

Example 5

In vitro Expression, Isolation and Purification of Recombinant RNA Binding Protein 33

Figure 1:
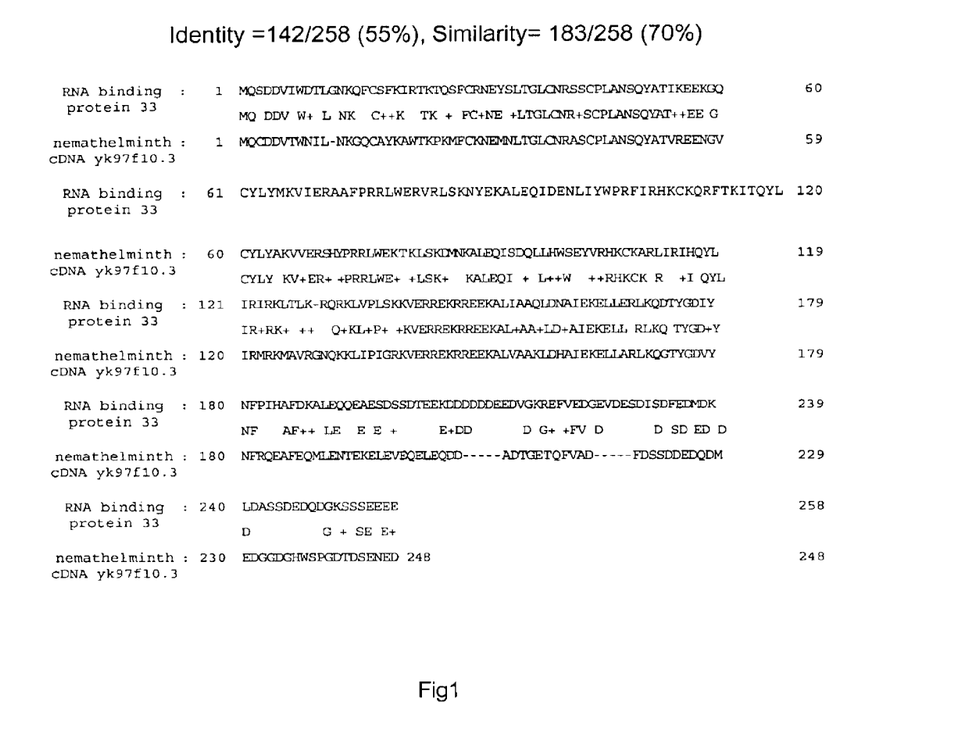
FIG. 1 shows an alignment comparison of amino acid sequences of RNA binding protein 33 of the invention and nemathelminth cDNA yk97f10.3, a member of human zinc finger protein Kruppel family. The upper sequence is RNA BINDING PROTEIN 33, and the lower sequence is nemathelminth cDNA yk97f10.3. The identical and similar amino acids are indicated by a one-letter code of amino acid and "+" respectively.

A pair of primers for specific amplification was designed based on SEQ ID NO: 1 and the encoding region in FIG. 1, the sequences are as follows:

Primer3:5'-CATCCATGGGCATGCAGTCGGATGATGTTATCTG-3' (SEQ ID NO: 5)

Primer4:5'-CCCGGATCCCCCGTGGTTTTGGCTTTGGCCAC-3' (SEQ ID NO: 6)

Figure 2:
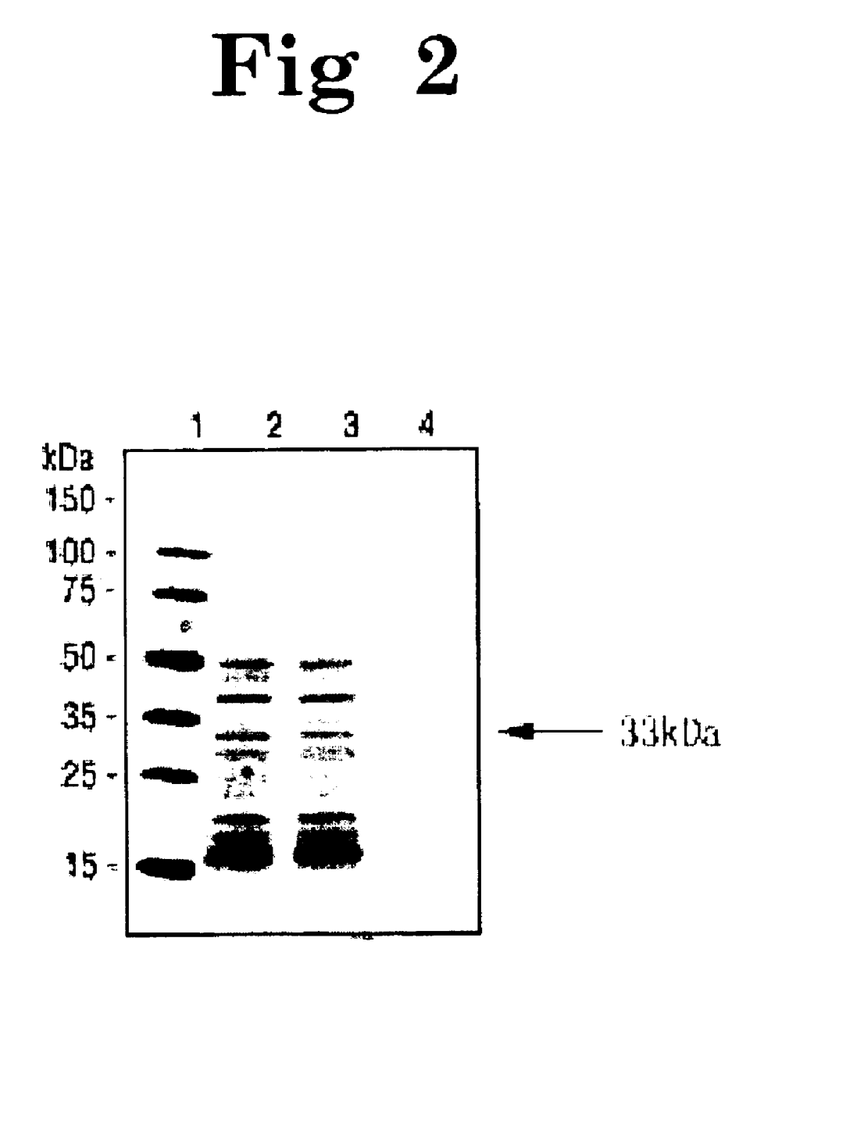
FIG. 2 shows the SD S-PAGE of the isolated RNA binding protein 33, which has a molecular weight of 33kDa. The isolated protein band is marked with an arrow.

These two primers contain a NcoI and BamHI cleavage site on the 5' end respectively. Within the sites are the coding sequences of the 5' and 3' end of the desired gene. NcoI and BamHI cleavage sites were corresponding to the selective cleavage sites on the expression vector pET-28b(+) (Novagen, Cat. No. 69865.3). PCR amplification was performed with the plasmid pBS-0196b12 containing the full-length target gene as a template. The PCR reaction was subject to a 50 µl system containing 10 pg pBS-0196b12 plasmid, 10 pmol of Primer-3 and 10 pmol of Primer-4, 1 µl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NcoI and BamHI, the large fragments were recovered and ligated with T4 ligase. The ligated product was transformed into *E. coli* DH5α with the calcium chloride method. After cultured overnight on a LB plate containing a final concentration of 30 ug/ml kanamycin, the positive clones were selected out using colony PCR and then sequenced. The positive clone pET-0196b12 with the correct sequence was selected out and the recombinant plasmid thereof was transformed into BL21 (DE3)plySs (Novagen) using the calcium chloride method. In a LB liquid medium containing a final concentration of 30 µg/ml of kanamycin, the host bacteria BL21(pET-0196b12) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—RNA binding protein 33 was obtained by a His.Bind Quick Cartridge (Novagen) affinity column with binding 6His-Tag. SDS-PAGE showed a single band at 33 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

Example 6 Preparation of Antibody against RNA Binding Protein 33

The following specific RNA binding protein 33 polypeptide was synthesized by a polypeptide synthesizer (PE-ABI): NH$_2$-Met-Gln-Ser-Asp-Asp-Val-Ile-Trp-Asp-Thr-Leu-Gly-Asn-Lys-Gln-COOH(SEQ ID NO:7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 µg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to RNA binding protein 33.

We claim:

1. An isolated polypeptide having and RNA binding protein 33 activity and comprising an amino acid sequence of SEQ ID No: 2.

2. An isolated polypeptide having an RNA binding protein 33 activity and comprising an amino acid sequence that is at least 95% identical to SEQ ID NO: 2.

3. A method for detecting a disease related to the polypeptide of claim 2, or for determining a susceptibility of a mammal thereto, said method comprising detecting the amount of expression of said polypeptide, or detecting the activity of said polypeptide.

4. A method for screening mimetics, agonists, antagonists or inhibitors of an RNA binding protein 33; or for peptide profiling, the method comprising labeling a polypeptide according to claim 2 and applying the labeled polypeptide in the screening or profiling.

5. A pharmaceutical composition comprising a polypeptide according to claim 2, and a pharmaceutically acceptable carrier.

* * * * *

SEQUENCE LISTING

```
<160> NUMBER OF SEQ ID NOS: 7

<210> SEQ ID NO 1
<211> LENGTH: 3473
<212> TYPE: DNA
<213> ORGANISM: Homo sapiens
<220> FEATURE:
<221> NAME/KEY: CDS
<222> LOCATION: (16)..(918)
<223> OTHER INFORMATION:
<220> FEATURE:
<221> NAME/KEY: misc_feature
<222> LOCATION: (3473)..(3473)
<223> OTHER INFORMATION: n is an unknown nucleotide

<400> SEQUENCE: 1
```

-continued

```
ggagccgcgg acacc atg cag tcg gat gat gtt atc tgg gat aca cta gga          51
               Met Gln Ser Asp Asp Val Ile Trp Asp Thr Leu Gly
                 1               5                  10 aac aag caa ttt tgt tcc ttc aaa ata aga acc aag act cag agc ttc           99
Asn Lys Gln Phe Cys Ser Phe Lys Ile Arg Thr Lys Thr Gln Ser Phe
         15                  20                  25 tgc cga aat gaa tat agc ctg act gga ctg tgt aat cgg tca tcc tgt          147
Cys Arg Asn Glu Tyr Ser Leu Thr Gly Leu Cys Asn Arg Ser Ser Cys
     30                  35                  40 ccc ctg gca aat agt cag tat gcc act att aaa gaa gag aaa gga cag          195
Pro Leu Ala Asn Ser Gln Tyr Ala Thr Ile Lys Glu Glu Lys Gly Gln
 45                  50                  55                  60 tgc tac ttg tat atg aag gtt ata gaa cga gcg gct ttt cct cgg cgt          243
Cys Tyr Leu Tyr Met Lys Val Ile Glu Arg Ala Ala Phe Pro Arg Arg
                 65                  70                  75 ctc tgg gaa cgg gtc cgg ctt agt aaa aac tat gag aaa gca ctg gag          291
Leu Trp Glu Arg Val Arg Leu Ser Lys Asn Tyr Glu Lys Ala Leu Glu
             80                  85                  90 caa ata gat gaa aat ctg att tac tgg ccc cgt ttc att cga cac aaa          339
Gln Ile Asp Glu Asn Leu Ile Tyr Trp Pro Arg Phe Ile Arg His Lys
         95                 100                 105 tgt aag cag aga ttc acc aag atc acc caa tac cta att cga att aga          387
Cys Lys Gln Arg Phe Thr Lys Ile Thr Gln Tyr Leu Ile Arg Ile Arg
    110                 115                 120 aaa ctt aca cta aag cga cag agg aaa ctt gtt cct ttg agt aag aag          435
Lys Leu Thr Leu Lys Arg Gln Arg Lys Leu Val Pro Leu Ser Lys Lys
125                 130                 135                 140 gtg gag cgt agg gag aaa aga aga gag gaa aag gca tta ata gct gct          483
Val Glu Arg Arg Glu Lys Arg Arg Glu Glu Lys Ala Leu Ile Ala Ala
                145                 150                 155 cag ctg gac aat gcc att gag aag gaa tta ctg gag aga ctg aaa caa          531
Gln Leu Asp Asn Ala Ile Glu Lys Glu Leu Leu Glu Arg Leu Lys Gln
            160                 165                 170 gat acg tat ggc gac atc tac aac ttc ccc att cat gcc ttc gac aaa          579
Asp Thr Tyr Gly Asp Ile Tyr Asn Phe Pro Ile His Ala Phe Asp Lys
        175                 180                 185 gcc ctg gaa caa cag gag gca gag agt gac tct tca gat act gag gaa          627
Ala Leu Glu Gln Gln Glu Ala Glu Ser Asp Ser Ser Asp Thr Glu Glu
    190                 195                 200 aaa gat gat gat gat gat gat gag gaa gat gtg ggg aaa aga gaa ttt          675
Lys Asp Asp Asp Asp Asp Asp Glu Glu Asp Val Gly Lys Arg Glu Phe
205                 210                 215                 220 gtc gaa gat ggt gag gta gat gag agt gac ata agt gat ttt gag gat          723
Val Glu Asp Gly Glu Val Asp Glu Ser Asp Ile Ser Asp Phe Glu Asp
                225                 230                 235 atg gat aaa ctg gat gcc agc agt gat gaa gat cag gat ggt aaa tcc          771
Met Asp Lys Leu Asp Ala Ser Ser Asp Glu Asp Gln Asp Gly Lys Ser
            240                 245                 250 tcc agt gag gag gag gaa gaa aag gcc ctt agt gcg aaa cac aaa ggc          819
Ser Ser Glu Glu Glu Glu Glu Lys Ala Leu Ser Ala Lys His Lys Gly
        255                 260                 265 aaa atg ccc ttg aga gga cca ctg cgg aga aaa cga gcc tat gtg gaa          867
Lys Met Pro Leu Arg Gly Pro Leu Arg Arg Lys Arg Ala Tyr Val Glu
    270                 275                 280 ata gaa tac gag cag gag aca gag ccc gtg gcc aaa gcc aaa acc acg          915
Ile Glu Tyr Glu Gln Glu Thr Glu Pro Val Ala Lys Ala Lys Thr Thr
285                 290                 295                 300 tga tttccctttc agcatttata cccaggactg aacatgcaga actgttttt              968 ttttttttttt ttatcttaaa cacatacaca cctccagttt ttgctctttt gtgttgtact    1028
```

-continued

```
gaacacaata tttgtgtttt tattatttat gccacgtcag tggggcaaga aatctggagt    1088
gagtgaagaa agctaagttg tgaacaagag tgtttttata gcatatgtgt tgaagtaaca    1148
gcttgtgccc gagaaactta acagatgagt tcttgaatct gggatgagat gacggatgta    1208
aatatttcta aatttttaaat gctacattac ttggtgtcct tttttttctcc caaactttat   1268 ttagaaatgg aaggagttca attttttctt gttctactt ccctattctt atggaggtaa     1328
aaggaaagaa ggaaggaaac cagcagcttt cacttacaaa gtttcgtgta aaaatatctt    1388
tttttcttaa ataactccat tcatacaaat tgggatggga agaaaatcct ttcctcttgg    1448
gaaagtaata caagtcttaa gttccattgt agggtgcgcc ttcagaaacc tgctgcactt    1508
ttctgatata gttcaccact tttctgtctt cacagctttg gggattttg gccaggagac     1568 cctgaaacat gaaaccaaac aggctttgat atttttttt tttttaatta ctttcccctt     1628
ttgcttgatt cttcttcctt ggtatcatat tcaaaggagg aaagaatgga tgacacttag    1688
ggacaggtca ctaagcagaa taggtattag ttggtttttt attatttta aatttatata     1748 gctctcatgt attgaaggtg ctactttaaa aactgtgtta atgtacttgc aaatctcctg    1808
ctggctcatg aaacagcaga attccagcca aggcaaattc agttggatct agggcttgaa    1868
aactgcccaa gattaaagag ctaagatgaa atagtttgaa taaactggta aaataacaat    1928
tcatactatc tctacatatt tttaggatat gaattttttt ttcctgctgg gtagattgtc    1988
cagtgactta tggcatgaat ttcttttcat gctaccttca atcttcaact aaagatttct    2048 aaaagggta agaaatgagg cagtagttta ttaaatacat agaagtacac agctattata    2108
tgctgtggct ttgagaagtt aacttttgtg gaatatgaaa ccaaaggaag aatttccatg    2168
tagataaatt aagaataggg aaaaacatct acctaaaaga tggttgtccc taaaaaactg    2228
gaaacatctg aaatgctcta tttatgttat tattcctggg agcttatagc ccattatttt    2288 tactttttttt tttaattcag aagactagaa cagaacttaa attttacaaa cttttgatca    2348
taatgctttt gcccatactg tctcgtcctt agccccagtg acatgtgctg atcctcctgc    2408
ctttagttct aaatggttca gaatagcttt aaaagatgaa taagaaaaaa gatcaagctc    2468
ttttgaggct agagggctca tatggagatc taaaaccctc catgttcatt tccagacttg    2528
gtcaggcaca tacatagtaa attataatca atcatgggaa ttacataagg ataatgaggc    2588
ccaactgaaa ccaagtttca gtctgcctta cctttacccg tccttgagaa cagcggtcca    2648
ggagaatcag gcagtctgtg gcctcctgta gcagggcgct cttacagact caggtgtaag    2708
gtttggatcc cttgctacat cacaaatcag tttcaagagg gccttcagta agaccacaag    2768
tctgcaggaa acttctggaa tcaggaagaa aagctatgtt catactctaa atctggatat    2828
taaaattgga agagactttc aaagactgtc aagtggaaag ctatcatttc ctaaattaag    2888
gaacttaggt caaagttaaa taaaaaagac ctaaaaacag aaccaaagtc agcctctaga    2948
tttcttaccc tcaagtctcc tgttagcata ctgcctatac acacagacac accctctgcc    3008
acactgctct cttccttcca gaagcttggt tctactataa gcaacagctc cttcatgggc    3068
tgagaagggg aaaccaggat ctccccaacc aagggcctat acttttattt ttcaactcta    3128
ttaactgaac tatgcttgga gagagccctg aatcctttaa ctttattgcc atcttaggcc    3188
tggaagttag agtgagggaa atgagcttgg cttctgggac tgtgtcaagt tgaattttct    3248
gtcatttaat ttcagatcct agctcatcat cagtgaagtc cagcctactt acttgtaact    3308
attaaccttt ctaaaagttt tcatcgccct ggtaaagctc cagaaatgga caatgctagt    3368
```

-continued

```
gactgcacaa tattgtgact gtacttaatg ccactgaact gtacacttta aaatggaaaa    3428
tttatatgta tttttaccac aataaacaaa aaacttaagc ggcgn                    3473
```

<210> SEQ ID NO 2
<211> LENGTH: 300
<212> TYPE: PRT
<213> ORGANISM: Homo sapiens

<400> SEQUENCE: 2

```
Met Gln Ser Asp Asp Val Ile Trp Asp Thr Leu Gly Asn Lys Gln Phe
  1               5                  10                  15

Cys Ser Phe Lys Ile Arg Thr Lys Thr Gln Ser Phe Cys Arg Asn Glu
                 20                  25                  30

Tyr Ser Leu Thr Gly Leu Cys Asn Arg Ser Ser Cys Pro Leu Ala Asn
             35                  40                  45

Ser Gln Tyr Ala Thr Ile Lys Glu Glu Lys Gly Gln Cys Tyr Leu Tyr
     50                  55                  60

Met Lys Val Ile Glu Arg Ala Ala Phe Pro Arg Arg Leu Trp Glu Arg
 65                  70                  75                  80

Val Arg Leu Ser Lys Asn Tyr Glu Lys Ala Leu Glu Gln Ile Asp Glu
                 85                  90                  95

Asn Leu Ile Tyr Trp Pro Arg Phe Ile Arg His Lys Cys Lys Gln Arg
                100                 105                 110

Phe Thr Lys Ile Thr Gln Tyr Leu Ile Arg Ile Arg Lys Leu Thr Leu
            115                 120                 125

Lys Arg Gln Arg Lys Leu Val Pro Leu Ser Lys Lys Val Glu Arg Arg
    130                 135                 140

Glu Lys Arg Arg Glu Glu Lys Ala Leu Ile Ala Ala Gln Leu Asp Asn
145                 150                 155                 160

Ala Ile Glu Lys Glu Leu Leu Glu Arg Leu Lys Gln Asp Thr Tyr Gly
                165                 170                 175

Asp Ile Tyr Asn Phe Pro Ile His Ala Phe Asp Lys Ala Leu Glu Gln
                180                 185                 190

Gln Glu Ala Glu Ser Asp Ser Ser Asp Thr Glu Lys Asp Asp Asp
        195                 200                 205

Asp Asp Asp Glu Glu Asp Val Gly Lys Arg Glu Phe Val Glu Asp Gly
210                 215                 220

Glu Val Asp Glu Ser Asp Ile Ser Asp Phe Glu Asp Met Asp Lys Leu
225                 230                 235                 240

Asp Ala Ser Ser Asp Glu Asp Gln Asp Gly Lys Ser Ser Ser Glu Glu
                245                 250                 255

Glu Glu Glu Lys Ala Leu Ser Ala Lys His Lys Gly Lys Met Pro Leu
            260                 265                 270

Arg Gly Pro Leu Arg Arg Lys Arg Ala Tyr Val Glu Ile Glu Tyr Glu
        275                 280                 285

Gln Glu Thr Glu Pro Val Ala Lys Ala Lys Thr Thr
    290                 295                 300
```

<210> SEQ ID NO 3
<211> LENGTH: 25
<212> TYPE: DNA
<213> ORGANISM: Artificial Sequence
<220> FEATURE:
<223> OTHER INFORMATION: (oligonucleotide primer)

<400> SEQUENCE: 3

```
ggagccgcgg acaccatgca gtcgg                                           25
```

```
<210> SEQ ID NO 4
<211> LENGTH: 25
<212> TYPE: DNA
<213> ORGANISM: Artificial Sequence
<220> FEATURE:
<223> OTHER INFORMATION: (oligonucleotide primer)

<400> SEQUENCE: 4
cgccgcttaa gtttttttgtt tattg                                              25

<210> SEQ ID NO 5
<211> LENGTH: 34
<212> TYPE: DNA
<213> ORGANISM: Artificial Sequence
<220> FEATURE:
<223> OTHER INFORMATION: (oligonucleotide primer)

<400> SEQUENCE: 5
catccatggg catgcagtcg gatgatgtta tctg                                     34

<210> SEQ ID NO 6
<211> LENGTH: 32
<212> TYPE: DNA
<213> ORGANISM: Artificial Sequence
<220> FEATURE:
<223> OTHER INFORMATION: (oligonucleotide primer)

<400> SEQUENCE: 6
cccggatccc ccgtggtttt ggctttggcc ac                                       32

<210> SEQ ID NO 7
<211> LENGTH: 15
<212> TYPE: PRT
<213> ORGANISM: Artificial Sequence
<220> FEATURE:
<223> OTHER INFORMATION: (partial sequence of SEQ ID NO.: 2)

<400> SEQUENCE: 7

Met Gln Ser Asp Asp Val Ile Trp Asp Thr Leu Gly Asn Lys Gln
1               5                   10                  15
```